(12) United States Patent
Stewart et al.

(10) Patent No.: US 9,340,595 B2
(45) Date of Patent: May 17, 2016

(54) CROSSLINKING WITHIN COORDINATION COMPLEXES

(75) Inventors: Russell John Stewart, Salt Lake City, UT (US); Patrick Franklin Kiser, Salt Lake City, UT (US); Richard Scott Stayner, Minneapolis, MN (US)

(73) Assignee: University of Utah Research Foundation, Salt Lake City, UT (US)

( * ) Notice: Subject to any disclaimer, the term of this patent is extended or adjusted under 35 U.S.C. 154(b) by 2155 days.

(21) Appl. No.: 10/567,992

(22) PCT Filed: Aug. 11, 2004

(86) PCT No.: PCT/US2004/025958
§ 371 (c)(1),
(2), (4) Date: Oct. 4, 2006

(87) PCT Pub. No.: WO2005/019421
PCT Pub. Date: Mar. 3, 2005

(65) Prior Publication Data
US 2010/0267005 A1    Oct. 21, 2010

Related U.S. Application Data

(60) Provisional application No. 60/494,349, filed on Aug. 11, 2003.

(51) Int. Cl.
| | | |
|---|---|---|
| C07K 1/04 | (2006.01) | |
| C12Q 1/00 | (2006.01) | |
| C12Q 1/26 | (2006.01) | |
| C12Q 1/28 | (2006.01) | |
| C07K 14/47 | (2006.01) | |
| C07K 1/107 | (2006.01) | |
| C07K 7/06 | (2006.01) | |
| C12Q 1/70 | (2006.01) | |
| C07K 7/04 | (2006.01) | |
| C07K 17/14 | (2006.01) | |

(52) U.S. Cl.
CPC .......... C07K 14/4716 (2013.01); C07K 1/1075 (2013.01); C07K 1/1077 (2013.01); C07K 7/06 (2013.01); *C07K 2319/21* (2013.01)

(58) Field of Classification Search
None
See application file for complete search history.

(56) References Cited

U.S. PATENT DOCUMENTS 6,077,371 A    6/2000   Lundstrom et al.
6,087,452 A    7/2000   Stewart et al.

OTHER PUBLICATIONS

Stayner RS, Min DJ, Kiser PF, Stewart RJ, "Site-Specific Cross-Linking of Proteins Through Tyrosine Hexahistidine Tags" Bioconjug Chem, Nov.-Dec. 2005, 16(6),pp. 1617-1623.*
Aeschbach, R. et al. *Biochim Biophys Acta* 439(2):292-301 (1976).
Bal, W.,et al., *Chem Res Toxicol* 13(7):616-624 (2000).
Boger, D.L. et al., *JACS* 116(19):8544-8556 (1994).
Brady, J.D., et al., *Biochem J* 315(Pt1):323-327 (1996).
Brown, K.C. et al., *Biochemistry* 34(14):4733-4739 (1995).

(Continued)

*Primary Examiner* — Thane Underdahl
*Assistant Examiner* — Aaron J Kosar
(74) *Attorney, Agent, or Firm* — Thorpe North & Western, LLP (57) ABSTRACT

Crosslinked proteins, proteins and polymers, and polymers and methods of making the same are disclosed. In one illustrative embodiment, a method is provided comprising the steps of attaching a chelator to one or more polymers; creating a coordination complex between the first protein, the second protein, and a metal ion; and crosslinking the first and second proteins by exposing the coordination complex to an oxidant.

32 Claims, 6 Drawing Sheets

(56) References Cited

OTHER PUBLICATIONS

Brown, K.C. et al., *Biochemistry* 37(13):4397-4406 (1998).
Burrows, C.J. et al., *Acta Chem Scand* 50(4):337-344 (1996).
Chen, L. et al., *Bioconjug Chem* 11(5):734-740 (2000).
Coyne, K.J. et al., *Science* 277(5333):1830-1832 (1997).
Dalle-Donne, I. et al., *American Biotechnology Laboratory* 19(13):34-36 (2001).
Eickhoff, H. et al., *Tetrahedron* 57(2):353-364 (2001).
Espin, J.C. et al., *Eur J Biochem* 267(5):1270-1279 (2000).
Fancy, D.A. et al., *Chem Biol* 3(7):551-559 (1996).
Fancy, D.A. et al., *Biochem Biophys Res Commun* 247(2):420-426 (1998).
Foerder, C.A. et al., *PNAS (USA)* 74(10):4214-1418 (1977).
Fry, S.C., *Biochem J* 204(2):449-455 (1982).
Gill, G. et al., *Chem Res Toxicol* 10(3):302-309 (1997).
Goldstein, S. et al., *J. Biol. Chemistry* 275(5):3031-3036 (2000).
Hickerson, R.P. et al., *J Mol Biol* 279(3):577-587 (1998).
Higashimura, H. et al., *J. Am. Chem. Soc.* 120:8529-8530 (1998).
Ho et al., *Lanmuir* 14:3889-3894 (1998).
Hom, L.G. et al., Biotechniques 25(1):20-22 (1998).
Jacob, J.S. et al., *J. Biol. Chemistry* 271(33):19950-19956 (1996).
Jung, G., *Letters in Peptide Science* 8(3-5):259-265 (2001).
Kagan, H.M. et al., *J Cell Biochem* 88(4):660-672 (2003).
LaBella, F. et al., *Biochem Biophys Res Commun* 26(6):748-753 (1967).
Malanik, V. et al., *Connect Tissue Res* 6(4): 235-240 (1979).
Malnar, I et al., *Tetrahedron Letters* 41(12):1907-1911 (2000).
McDowell, L.M. et al., *J Biol Chem* 274(29):20293-20295 (1999).
Michon, T. et al., *Biochemistry* 36(28):8504-8513 (1997).
Monzani, E. et al., *Inorganic Chemistry* 37:553-562 (1998).
Muller, J.G. et al., *J Inorg Biochem* 54(3):199-206 (1994).
Nishiyama, S. et al., *Tetrahedron Letters* 35(45):8397-8400 (1994).
Oudgenoeg, C. et al., *J. Agric. Food Chem.* 49(5):2503-2510 (2001).
Pennathur, S. et al., *J. Biol. Chemistry* 274(49):34621-34628 (1999).
Person, M.D. et al., *Protein Sci* 10(8)1549-1562 (2001).
Qin, XX et al., *J Biol Chem* 272(51):32623-32627 (1997).
Qin, XX et al., *PNAS (USA)* 95(18):10517-10522 (1998).
Raven, D.J. et al., *Biochim Biophys Acta* 251(1):96-99 (1971).
Rzepecki, L.M. et al., *Mol Mar Bid Biotechmol* 1(1):78-88 (1991).
Sanchez-Ferrer, A. et al., *Biochim Biophys Acta* 1247(1):1-11 (1995).
Souza, J.M. et al., *J. Biol. Chemistry* 275(24):18344-18349 (2000).
Spikes, J.D. et al., *Photochemistry and Photobiology* 69:34s- (1999).
Stemmler, A.J. et al., *JACS* 121(29):6956-6957 (1999).
Thurston, C.F., *Microbiology* 140:19-26 (1994).
Vaccaro, F. et al., *Biomacromolecules* 2(3):906-911 (2001).
Wang et al., *Nature* 397:417-420 (1999).
Fancy et al.; "Scope, Limitations and Mechanistic Aspects of the Photo-Induced Cross-Linking of Proteins by Water-Soluble Metal Complexe"; Chem. Biol.; 2000; pp. 697-708; vol. 7.

* cited by examiner

CROSSLINKING WITHIN COORDINATION COMPLEXES

GOVERNMENT INTEREST

This invention was made with government support under GM049860 awarded by the National Institutes of Health and BES9807287 awarded by the National Science Foundation. The government has certain rights in the invention.

BACKGROUND AND SUMMARY OF THE INVENTION

Complex networks of highly crosslinked biopolymers are common materials in living tissues. Familiar examples of these are the networks of collagen fibers that form the matrices of skin, bones, and connective tissues. The crosslinking found in these materials gives them their tensile strength, elasticity, and other valuable characteristics. In nature, the crosslinking, which is so critical to the function of these tissues, is accomplished by enzymatic oxidation of specific amino acid side chains of the protein materials involved, thus creating reactive intermediates which spontaneously form crosslinks. In the case of collagen and elastin, the $\epsilon$-amino group of specific lysine residues are oxidatively deaminated by lysyl oxidase into reactive aldehyde groups that spontaneously condense with neighboring peptidyl aldehydes or $\epsilon$-amino groups (Kagan, H. M. et al., *J Cell Biochem*, 2003. 88(4): p. 660-72).

Another widely occurring mechanism of biomolecule crosslinking is oxidative coupling through phenols. Examples are the formation of lignin, which is a major structural component of plant cell walls, the formation of melanin pigments, the curing of tree sap into hard lacquers, the formation of peptidic natural products that exhibit high biological activity, such as vancomycin (Jung, G., *Letters in Peptide Science*, 2001. 8(3-5): p. 259-265; Malnar, I. et al. *Tetrahedron Letters*, 2000. 41(12): p. 1907-1911; Nishiyama, S., et al., *Tetrahedron Letters*, 1994. 35(45): p. 8397-8400) and bouvardin (Boger, D. L., et al. *JACS*, 1994. 116(19): p. 8544-56), through the formation of dityrosine protein crosslinks. Dityrosine protein linkages have been found in many structural proteins including elastin (LaBella, F., et al., *Biochem Biophys Res Commun.*, 1967. 26(6): p. 748-53; Malanik, V. et al., *Connect Tissue Res*, 1979. 6(4): p. 235-40), silk (Raven, D. J., C. Earland, et al., *Biochim Diophys Acta*, 1971. 251(1): p. 96-99), plant cell wall extensin (Fry, S. C., *Biochem J*, 1982. 204(2): p. 449-55; Brady, J. D., et al. *Biochem J*, 1996. 315(Pt 1): p. 323-7), and in hardened fertilization membranes of insect and sea urchin eggs (Foerder, C. A. et al., *PNAS (USA)*, 1977. 74(10): p. 4214-8). These oxidative phenolic coupling processes are catalyzed by a large number of structurally and mechanistically distinct metalloenzymes, including peroxidases, tyrosinases, and laccases. Peroxidases crosslink tyrosines by extracting a single electron from the phenol side chain to create a radical that then reacts with a vicinal phenol side chain to form dityrosine or isodityrosine (Michon, T., et al., *Biochemistry*, 1997. 36(28): p. 8504-13; Eickhoff, H., et al., *Tetrahedron*, 2001. 57(2): p. 353-364). Tyrosinases may crosslink tyrosine residues in two steps: first, the phenol side chain is hydroxylated forming 3,4-dihydroxyphenyl-L-alanine (DOPA); second, DOPA is further oxidized to form reactive o-quinones that spontaneously crosslink (Sanchez-Ferrer, A., et al., *Biochim Biophys Acta*, 1995. 1247(1): p. 1-11; Espin, J. C., et al., *Eur J Biochem*, 2000. 267(5): p. 1270-9).

These natural oxidative protein crosslinking mechanisms are mediated by transition metal-peptidyl coordination complexes. The redox active metal complexes come in many forms. Lysyl oxidase contains a single copper (II) atom and an organic co-factor formed by the intermolecular crosslinking of a lysine $\epsilon$-amine and a tyroxyl quinone (Kagan, H. M. et al., *J Cell Biochem*, 2003. 88(4): p. 660-72). Tyrosinases (Sanchez-Ferrer, A., et al., *Biochim Biophys Acta*, 1995. 1247 (1): p. 1-11) and laccases (Thurston, C. F., *Microbiology*, 1994. 140: p. 19-26) are multi-copper enzymes that transfer electrons to molecular oxygen. Peroxidases that crosslink tyrosines are iron-heme proteins that transfer single electrons from phenols to $H_2O_2$ (Michon, T., et al., *Biochemistry*, 1997. 36(28): p. 8504-13; Oudgenoeg, C., et al., *J. Agric. Food Chem.*, 2001. 49(5): p. 2503-10). Nature has found many distinct metal-mediated pathways for extracting electrons to crosslink phenolic compounds.

Another particularly intriguing example of crosslinking through tyrosine derivatives occurs in mussel byssal threads, which are specialized ligaments that bond the animals to an external substrate. The byssal threads contain several proteins and are heavily diDOPA crosslinked (Rzepecki, L. M., et al., *Mol Mar Bid Biotechmol*, 1991. 1(1): p. 78-88; McDowell, L. M., et al., *J Biol Chem*, 1999. 274(29): p. 20293-5). The thread proteins include three unusual collagens with blocky primary structures; a central collagen block is flanked by either elastin-like blocks (pre-ColP) (Coyne, K. J., et al., *Science*, 1997. 277(5333) p. 1830-2), silk-like blocks (pre-ColD) (Qin, X X., et al., *J Biol Chem*, 1997. 272(51): p. 32623-7), or amorphous glycine-rich blocks (pre-ColNG) (Qin, X X. et al., *PNAS (USA)*, 1998. 95(18): p. 10517-22). All three have histidine- and DOPA-rich domains at the amino- and carboxyl-termini. The histidine blocks likely chelate the several metal ions found associated with byssal threads. Chelate complexes are thought to participate in non-covalent intermolecular crosslinking of the collagens (Vaccaro, F. et al., *Biomacromolecules*, 2001. 2(3): p. 906-11).

Chelated transition metal ions, particularly Ni(II), can participate in oxidative crosslinking of biomolecules. Much of the research in this area has been done from the perspective of understanding nickel toxicity, which may be largely due to its oxidative activity when chelated by peptides, proteins, or nucleic acids (Gill, G., et al., *Chem Res Toxicol*, 1997. 10(3): p. 302-9; Bal, W., et al., *Chem Res Toxicol*, 2000. 13(7): p. 616-24). A second area of research has focused on creating synthetic catalysts that mimic metalloenzymes. For example, tyrosinase model complexes have been synthesized that are capable of regiospecific oxidation of phenol and catechol (Monzani, E., et al. *Inorganic Chemistry*, 1998. 37: p. 553-562) and regiospecific polymerization of phenol into poly(1, 4-phenylene oxide) (Higashimura, H., et al. *J. Am. Chem. Soc.*, 1998. 120: p. 8529-8530). A third area of research has been directed at exploiting the oxidative activity of chelated Ni(II) to create reagents for in vitro conjugation, crosslinking, or cleavage of biomolecules. A number of metal complexes have been synthesized that specifically modify DNA (Muller, J. G., et al., *J Inorg Biochem*, 1994. 54(3): p. 199-206; Burrows, C. J., et al., *Acta Chem Scand*, 1996. 50(4): p. 337-44; Hickerson, R. P., et al., *J Mol Biol*, 1998. 279(3): p. 577-87; Stemmler, A. J. et al.: *JACS*, 1999. 121(29): p. 6956-6957).

With regard to protein modification, others have found that Ni(II) complexed by the tripeptide $NH_2$-Gly-Gly-His (GGH) in the presence of the relatively strong oxidant monoperoxyphthalic acid (MMPP) crosslinked proteins known to associate in solution (Brown, K. C., et al., *Biochemistry*, 1995. 34(14): p. 4733-9). Subsequently, GGH genetically appended to the dimeric protein, ecotin, mediated intermolecular crosslinking between tyrosine residues in the presence of MMPP and Ni(II) (Brown, K. C., et al., *Biochemistry,* 1998. 37(13): p. 4397-406). Crosslinking between wild-type ecotin, in which tyrosine residues at the dimer interface are separated by 20 Å, was relatively inefficient (15%). By placing tyrosine residues within 5 Å of one another at the dimer interface, crosslinking efficiency was increased to 60%. This demonstrated a major advantage of protein crosslinking mediated by peptide metal complexes, that a redox active Ni(II) chelator and target tyrosine residues can be genetically positioned within a protein, creating the potential for site specific protein modification through oxidative conjugation or crosslinking. A recent report, however, revealed that this chemistry is much more complex than just dityrosine formation. A number of reactions occur in the strong oxidizing environment, and crosslinking between the terminal GG residues and tyrosine is one of the major reactions (Person, M. D., et al., *Protein Sci,* 2001. 10(8): p. 1549-62).

The $His_6$ tag (SEQ ID NO:1) commonly used for purification of recombinant proteins by immobilized metal affinity chromatography (IMAC) has also been shown to be redox active in the presence of nickel(II) and peracid oxidants. HIS-tagged glutathione S-transferase (H6GST (SEQ ID NO:2)), a dimer in solution, was covalently crosslinked in the presence of Ni(II) and MMPP (Fancy, D. A., et al., *Chem Biol,* 1996. 3(7): p. 551-9). Proteins that do not naturally associate with H6GST were not crosslinked, demonstrating that His6-mediated crosslinking does not proceed through a highly diffusible reactant and crosslinking is localized to the vicinity of the His6 tag. Going further, the same research group demonstrated that, in the presence of MMPP and Ni(II), H6GST mediated the formation of dityrosine from free tyrosine, that the mutagenic removal of tyrosine residues from H6GST decreased crosslinking efficiency, and that chemical addition of tyrosine residues using the Bolton-Hunter reagent increased crosslinking efficiency (Fancy, D. A., et al., *Biochem Biophys Res Commun,* 1998. 247(2): p. 420-26). The primary interest of this research appears to be the architectural analysis of multi-protein complexes.

A large and successful industry has grown up around the development of reagents for the post-translational chemical modification of proteins. Despite the ingenious variety of reagents and methods available, there is a continuing need for new protein technologies that grows in proportion to the increasing importance of proteins in several major industries, including pharmaceutics, clinical diagnostics, chemicals, energy, agriculture, environmental protection, food, and textiles processing. New and better tools for labeling, conjugating, crosslinking, and immobilizing proteins would be valuable in all of these industries. The expanding industrial use of proteins, driven by new protein technologies, may have profound effects on human health, ranging from more cost effective pharmaceuticals to decreased environmental and the consequent human health impact from the production of chemicals and energy.

In particular, methods are desired for crosslinking proteins, polymers, and/or other moieties, including those that are not naturally associated, illustratively in a manner that is predictable. Accordingly, a method of crosslinking proteins (such as enzymes), polymers (including biopolymers such as protein, polysaccharide, poly-nucleic acid, lipid, and synthetic polymers such as polyethylene glycol, ("PEG"), polypropylene glycol, polyesters, and polymeric surfaces (such as pluronics)), and/or other moieties (such as fluorescent compounds, small molecules illustratively having a molecular weight from 50 g/mol to 800 g/mol, and small molecules having a degree of polymerization from 1 to about 10), by contact with an oxidant after associating the two species to be linked in a coordination complex with a metal ion or ions is provided. Such a method is useful in a variety of applications, including the labeling of proteins, PEGylating proteins, coupling proteins and polymers, and affixing proteins to surfaces. In some embodiments, the method comprises a method of crosslinking a first and a second protein comprising the steps of attaching a metal-binding peptide, illustratively a HY-tag, to the first protein using methods known in the art; attaching a metal-binding peptide to the second protein using methods known in the art; forming a coordination complex between the first protein, the second protein, and a metal ion; and crosslinking the first and second proteins by exposing the coordination complex to an oxidant. In illustrative embodiments of the instant invention, the metal ion is selected from the group consisting of nickel, copper, cobalt, gadolinium, iron, osmium, palladium, rhodium, ruthenium, samarium, selenium, silver, strontium, tantalum, thulium, tin, tungsten, vanadium, yttrium, and zinc. In others, the metal ion may be a first row transition metal ion. The methods of this invention may be used for crosslinking any combination of proteins, polymers, and small molecules.

An oxidizing agent is a chemical reagent that is an oxidizer, or which promotes the oxidation of a desired reagent. In some embodiments of the invention, MMPP is used to promote the oxidation of tyrosine residues. Other oxidants have been found suitable as well, including peroxides, other peracids, oxidizing enzymes such as tyrosinase, oxygen, and other weaker oxidants, wherein a "weaker oxidant" is weaker than MMPP. In some embodiments, however, a stronger oxidant may be used. Illustratively, the oxidizing agent may be generated from an electrode surface. In one embodiment, the electrode surface is coated with a synthetic or natural polymer. $Na_2SO_3$ may also be used. While not itself an oxidant, $Na_2SO_3$ auto-oxidizes in the presence of complexed NiH to persulfate ($SO_5$). In another embodiment, the oxidizing agent may be activated by a metalloenzyme, including but not limited to a peroxidase, a tyrosinase, a laccase, and a catechol oxidase. One suitable metalloenzyme is horseradish peroxidase.

In some embodiments, the ligand used to create the coordination complex is a metal-binding peptide or metal chelating tag, such as an HY-tag. In illustrative embodiments of the instant invention, the HY-tag is chosen from a group of sequences that comprise about four to ten histidine residues and a number of tyrosine residues. The sequences largely differ from each other in the placement of the tyrosines. As used herein, the term HIS-tags refers to HIS-tags generally, while HIS-TYR tags or HY-tags refer to HIS-tags that include tyrosines therein. Either may be referred to as $his_6$-tags when the number of histidine residues is specified. Also, it is understood that while HY-tags are used in illustrative embodiments, other chelating constructs comprised of amino acids and/or other natural or synthetic monomers may be used, illustratively including tyrosine, dihydroxyphenylalanine, or other phenolic groups. It is understood that phenolic groups includes compounds having one or more aromatic benzene rings having one or more hydroxyl groups (—OH). In addition, phenolic derivatives, including oxidized forms of phenolic groups, may be used. Phenolic groups and phenolic derivatives may contain further substituents on the benzene ring in addition to the hydroxyl group(s).

Some of the embodiments of the invention may comprise methods for labeling proteins, as when a fluorescent label (illustratively fluorescein, rhodamine, CY-3, and CY-5), enzyme, or other molecule is attached. Other such molecules could include biotin, digoxigenin, polyethylene glycol, pluronics, and other suitable labels. In one embodiment, the second moiety can be a small molecule. In one aspect, the small molecule can have a molecular weight from 50 g/mol to 800 g/mol. In another aspect, the small molecule can be an oligomer with a degree of polymerization from 1 to 10. In still another aspect, the small molecule can be comprised of epitope labels or fluorophores, including those selected from the group consisting of digoxigenin, biotin, fluorescein, rhodamine, CY-3, CY-5, and derivatives thereof.

In some embodiments, the invention comprises a method of conjugating a protein with a synthetic polymer comprising the steps of attaching a HY-tag to a selected protein; attaching a HY-tag or other metal-chelating group containing or in close proximity to a phenolic functional group to a selected polymer; forming a coordination complex between the protein, the polymer, and a metal ion; and crosslinking the protein and polymer by exposing the coordination complex to an oxidant. In various of these embodiments, the polymer is a synthetic polymer. In some, the polymer is polyethylene glycol. In others, the polymer is chosen from the group of polyacrylates, polymer surfaces such as pluronics, carbohydrates such as dextran, and lipids. In still other embodiments, HY-tags, which may be the same or different, are used to link two polymers.

Other embodiments of the instant invention comprise methods of immobilizing a protein or other moiety on a polymer surface under conditions that preserve protein structure and activity, comprising the steps of modifying a polymeric surface such that the polymeric surface comprises a synthetic chelator; attaching a HY-tag to a protein; forming a coordination complex between the polymeric surface, the protein, and a metal ion; and immobilizing the protein to the polymeric surface by exposing the coordination complex to an oxidant, thus causing the crosslinking of the polymer and the protein. In some embodiments, the polymer surface is further comprised of a synthetic polymer. In others, the polymer is polyethylene glycol. In still others, the polymer is a pluronic.

Similarly, the moiety may already be immobilized on a solid surface and the method may be used to link a second moiety to the surface. Examples of solid surfaces include tissues, polymers, metals, ceramics, composites, biopolymers, bioceramics (such as bones and teeth), and colloidal particles. Colloidal particles illustratively include materials gold, silver, silica, semiconductors, fluorescent semiconductors, polystyrene, polymeric micelles, dendrimers, liposomes, and viruses, and may be of any size, illustratively of from 1 nm to 100 µm. The polymer may be coated onto or otherwise bound to the solid surface. It is also understood that the methods of this invention may be used to link two different surfaces together, wherein each of the two moieties is immobilized on its respective surface. Illustratively, this may be useful when each of the surfaces is a tissue, and the crosslinking may function as a surgical glue.

While targets catalyzed by the mildest possible oxidant, illustratively $O_2$, are desired for use with proteins that are particularly sensitive to oxidation, it is understood that stronger oxidants may be used in some instances, and that the metal complex may be selected accordingly. Also, while tyrosines are used to crosslink through dityrosine formation, other phenolic residues may be used and crosslinking may occur through a substituted bis-phenol adduct.

Various features and embodiments of the instant invention are useful for a variety of common research and medical applications. One of these is use in the formation of hydrogels. The ability to provide predictable crosslinking of the proteins in such gels could allow the formation of new types of gels with unique properties and characteristics. This application could also be used to encapsulate cells, proteins, and DNA for preservation and use. A related application would be use of the invention as a surgical glue. Such a glue could be composed of specifically-chosen proteins selected for ability to prevent or avoid an immune response, promote growth and regeneration of surrounding tissue, degrade over time, or exhibit any other possible characteristic. Additionally, the glue could be applied in a liquid form to the wound, and then the glue could be cured and the wound sanitized simultaneously by the application of hydrogen peroxide as an oxidant/sterilant. Many other uses are possible.

These and other objects, features, and advantages of the present invention will become more fully apparent from the following description and appended claims, or may be learned by the practice of the invention as set forth hereinafter.

BRIEF DESCRIPTION OF THE DRAWINGS

FIG. 1A shows all of the component parts, FIG. 1B shows chelation of the metal by both the HY-tagged protein and the substrate, FIG. 1C represents oxidation of the tyrosine, and FIG. 1D shows the dityrosine crosslink.

DETAILED DESCRIPTION OF THE INVENTION

The presently preferred embodiments of the present invention will be best understood by reference to the following more detailed description of the embodiments of the apparatus, system, and method of the present invention. This detailed description is not intended to limit the scope of the invention, as claimed, but is merely representative of presently preferred embodiments of the invention.

Figure 1A:
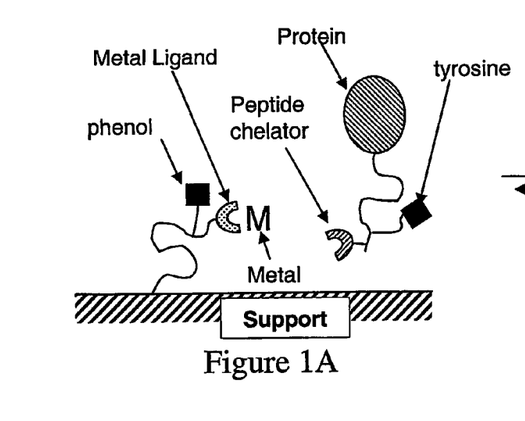
FIGS. 1A-D are a schematic representation of attachment of a HY-tagged protein to a substrate followed by oxidative formation of a dityrosine crosslink between the protein and the substrate.
Figure 1B:
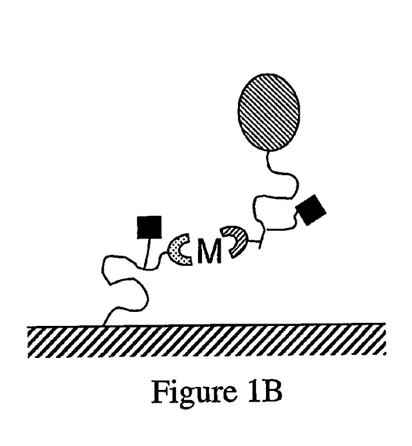
Figure 1C:
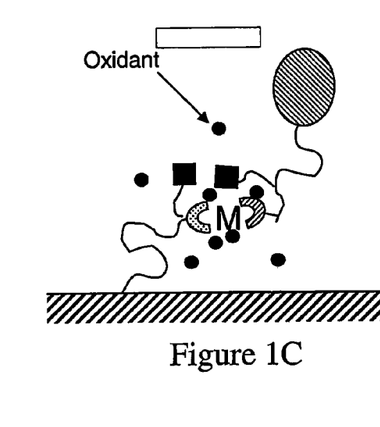
Figure 1D:
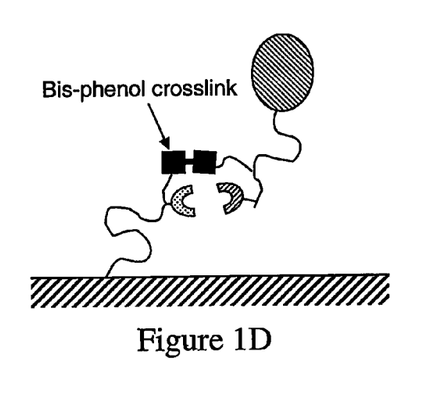

FIGS. 1A-D illustrate attachment of a HY-tagged protein to a substrate followed by oxidative formation of a dityrosine crosslink between the protein and the substrate. As illustrated in FIG. 1B, the conjugation site is pre-established as a complex before chemically reactive groups are created by an oxidant, illustratively a mild oxidant (FIG. 1C). The conjugation site itself catalyzes the creation of the reactive species, which localizes covalent bond formation to an intended region (FIG. 1D). As illustrated, random modifications that may damage or inactivate the target protein are limited. Further, the conjugation site on the protein may be genetically encoded in the form of a metal chelating peptide. Such a target protein would not require purification to be modified; it can be modified within a complex mixture of proteins. One advantage for protein array applications is that recombinant proteins may be selectively captured onto a solid support from a crude lysate of cells expressing the protein, and this can be done without purification and post-translational chemical modification.

Figure 2:
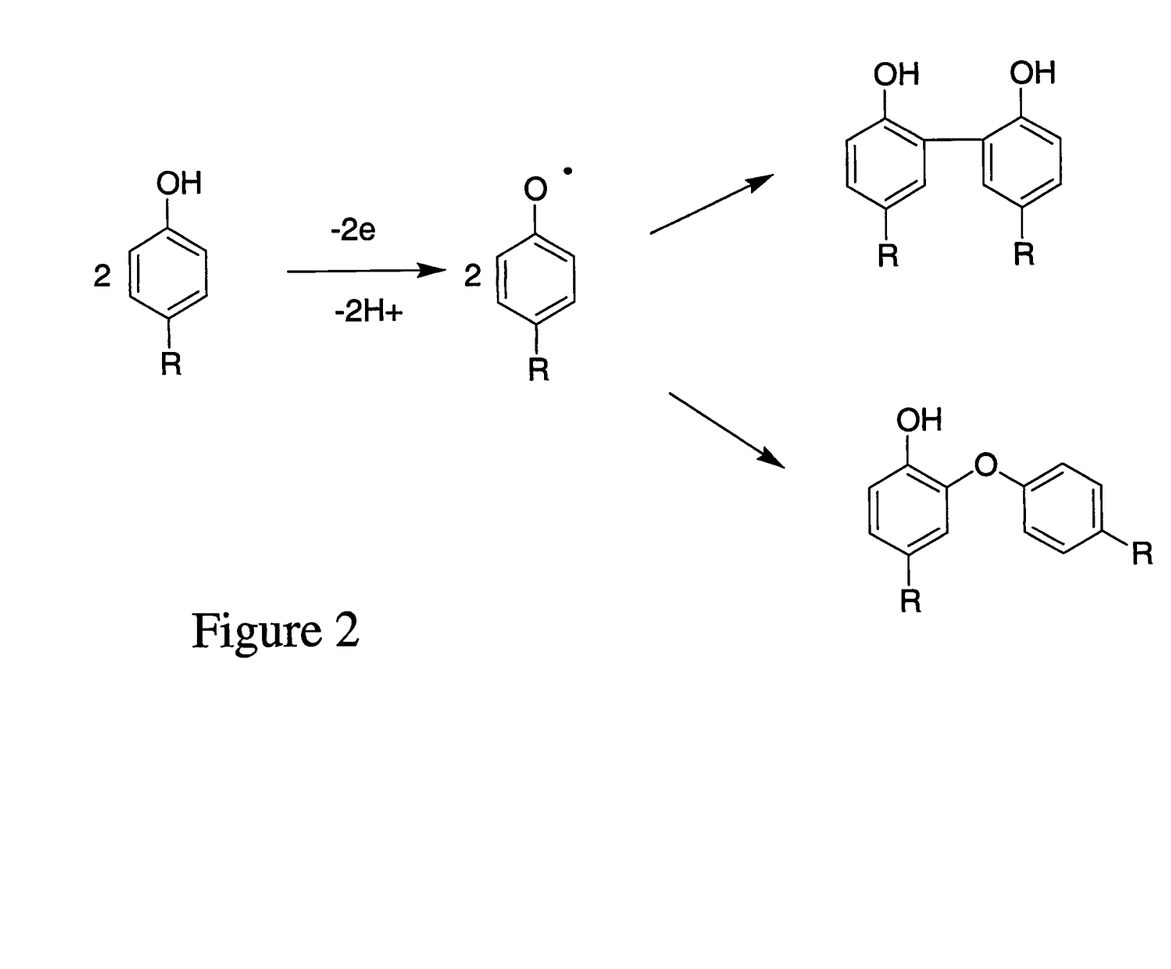
FIG. 2 shows phenol oxidation to two bis-phenolic species.

The radical homo-coupling of peptidyl tyrosine to form dityrosine is an irreversible process that leads to intermolecular crosslinks. The reaction proceeds at physiological pH through the formation of tyroxyl radicals by abstraction of a hydrogen atom from the hydroxyl group of tyrosine by a variety of oxidants (Eickhoff, H., et al., *Tetrahedron*, 2001. 57(2): p. 353-364; Dhirigra, O. P., *Intramolecular Oxidative Coupling of Aromatic Substrates*, in *Oxidation in* ORGANIC CHEMISTRY, W. S. Trahanovsky, Editor. 1982, Academic Press: New York). Dityrosine is formed by recombination of two of these tyroxyl radicals (FIG. 2) (Pennathur, S., et al., *J. Biol. Chemistry*, 1999. 274(49): p. 34621-34628; Jacob, J. S., et al., *J. Biol. Chemistry*, 1996. 271(33): p. 19950-19956; Spikes, J. D., et al., *Photochemistry and Photobiology*, 1999. 69: p. 84s-84s; Goldstein, S., et al., *J. Biol. Chemistry*, 2000. 275(5): p. 3031-3036; Souza, J. M., et al., *J. Biol. Chemistry*, 2000. 275(24): p. 18344-18349). As shown in FIG. 2, in the absence of a base, tyrosine undergoes a one-electron oxidation to give the cation radical. This species rapidly deprotonates to the neutral phenoxyl radical, which then reacts with another phenoxyl to form dityrosine. Several reaction pathways exist, however two predominant isomers of dityrosine have been identified, 3,3'-dityrosine (dityrosine) and 3-[4'-(2-carboxy-2-aminoethyl)phenoxy]tyrosine or (isodityrosine).

Because of the instability of the radical species involved, the structure of reaction intermediates and mechanisms of chemical transformations remain hypothetical and are often deduced from the structure of the identified products of the oxidation. The generation of the tyroxyl radical occurs at +1.2 V versus SCE. At this potential, many oxidizing agents are thermodynamically capable of generating the tyroxyl radical. Metal catalysts for this reaction are known and comprise $FeCl_3$, potassium hexacyanoferrate(III) under aqueous conditions, $Ag_2O$, $NiO_2$, $Ce^{+4}$. In addition, electrochemical oxidations have been reported (Eickhoff, H., et al., *Tetrahedron*, 2001. 57(2): p. 353-364; Dhirigra, O. P., *Intramolecular Oxidative Coupling of Aromatic Substrates*, in *Oxidation in Organic Chemistry*, W. S. Trahanovsky, Editor. 1982, Academic Press: New York).

Nickel(II) mediated association of proteins through his-tags has been reported (Horn, L. G., et al., *Biotechniques*, 1998. 25(1): p. 20-22). Thus, as an initial approach to investigating chelated metal-mediated protein crosslinking, tyrosine residues were genetically placed within and around $his_6$ tags on a model protein, a monomeric titin I28 Ig domain (Chen, L., et al., *Bioconjug Chem*, 2000. 11(5): p. 734-40). In the presence of Ni(II) and MMPP, HIS-tagged I28 domains with tyr residues between the HIS-tag and titin domain were efficiently crosslinked (Example 1). Those with tyr residues outside of the HIS-tags and the no tyr control did not crosslink.

EXAMPLES

Example 1

Chelator Synthesis

Figure 3A:
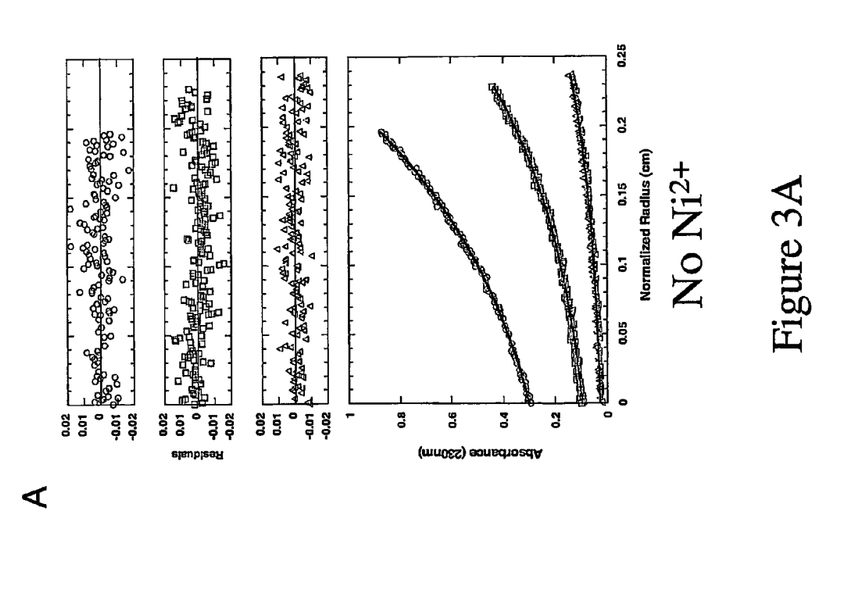
FIG. 3A shows sedimentation equilibrium data for H6GY-titin I28 (SEQ ID NO:6) protein without $Ni^{+2}$. The lower panels show experimental data points for 3 different loading concentrations of each protein with the corresponding calculated curve fit (solid line). The $H_6$GY-titin I28 protein is fit to a monomer model, MW=12.3±1 kDa. The upper panels show the residuals for these fits, all are small and random indicating a good fit.
Figure 3B:
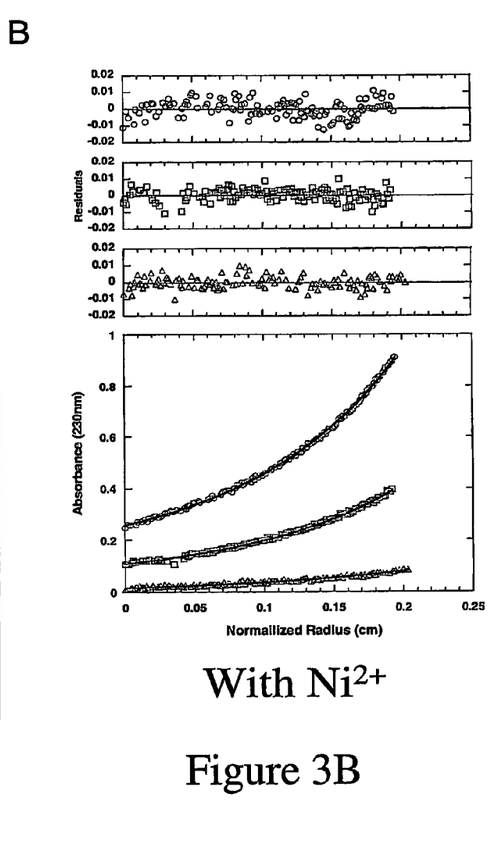
FIG. 3B shows sedimentation equilibrium data for $H_6$GY-titin I28 (SEQ ID NO:6) protein with a ten fold molar excess of $Ni^{+2}$. The lower panels show experimental data points for 3 different loading concentrations of each protein with the corresponding calculated curve fit (solid line). The $H_6$GY-titin I28 protein with a ten fold molar excess of $N^{+2}$ is fit to a monomer-dimer equilibrium $K_D$ of approximately 200 µM. The upper panels show the residuals for these fits, all are small and random indicating a good fit.

Two I28 proteins—proteins from an Ig domain of the muscle protein titin—were crosslinked though HIS-tags containing tyrosine residues. Tyrosine residues were placed within and around $his_6$-tags on a model protein, a monomeric titin I28 Ig domain, as shown in Table I, below. In the presence of NO) and MMPP, HIS-tagged I28 domains with tyr residues between the his-tag and titin domain were efficiently crosslinked (FIG. 3, lanes 4, 5). Those with tyr residues outside of the HIS-tags (lanes 1-3, 6, 7) and the no tyr control (lane 8) did not crosslink.

Figure 4:
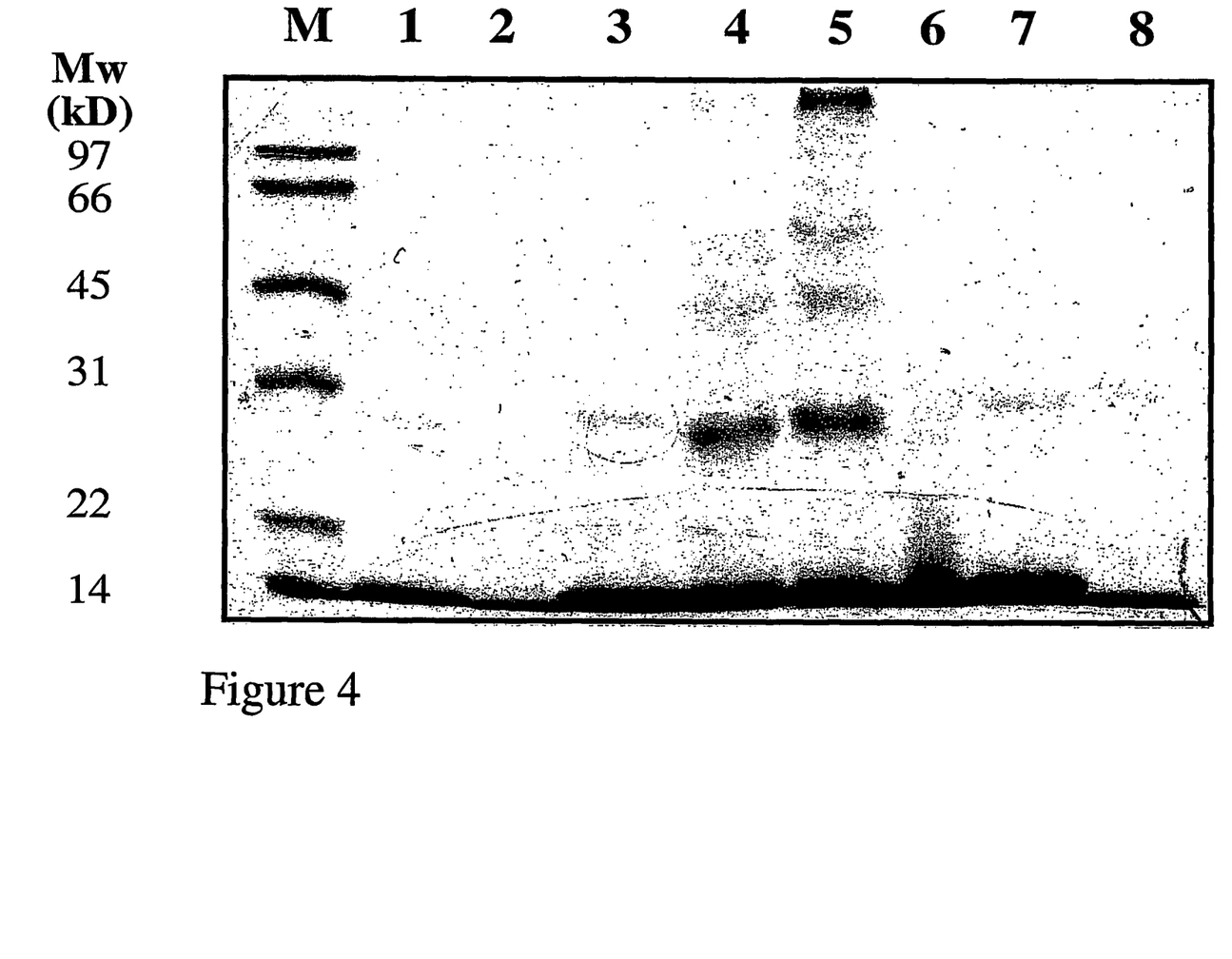
FIG. 4 is a gel showing the results of crosslinking of I28 domains with HY-tags; lane 1: $YH_6$-I28 (SEQ ID NO:3), lane 2: $YGH_6$-I28 (SEQ ID NO:4), lane 3: $YGYGH_6$-I28 (SEQ ID NO:5), lane 4: $H_6$GY-I28 (SEQ ID NO:6), lane 5: $H_6$GYGY-I28 (SEQ ID NO:7), lane 6: $YGH_6$GY-I28 (SEQ ID NO:8); lane 7: H3GYG $H_3$-I28 (SEQ ID NO:9), lane 8: no tyr control.

A convenient method to detect and monitor dityrosine formation is to measure its characteristic fluorescence at 410 nm (Aeschbach, R., et al., *Biochim Biophys Acta*, 1976. 439(2): p. 292-301; Dalle-Donne, I., et al., *American Biotechnology Laboratory*, 2001. 19(13): p. 34-36). This detection method was used to detect dityrosine formation using the HIS-tagged-I28 constructs discussed above, but using Ni(II) and sodium sulfite. The reactions took place within minutes in water, at near neutral pH, and under conditions that are biocompatible. That the HY-I28 proteins were crosslinked by dityrosine in the presence of this mild oxidant is confirmed by analyzing fluorescence emission spectra after treatment with Ni(II) and sodium sulfite (FIG. 4). Consistent with the electrophoresis results, only $H_6GY$-I28 (SEQ ID NO:6) and $H_6GYGY$-I28 (SEQ ID NO:7) fluoresced significantly at 410 nm (Table I). In the absence of Ni(II) or oxidant, no dityrosine was formed. Likewise, the control protein with no tyrosine in the $his_6$-tag did not fluoresce when treated with Ni(II) and sodium sulfite. Thus, with properly constructed HY-tags, crosslinking can occur in the presence of a mild oxidant.

TABLE I normalized dityrosine fluorescence (410nm) of His-tyr-tagged I28 proteins.

| HIS-tag | | Conditions | |
|---|---|---|---|
| | | $Ni(II)/Na_2SO_3$ | $Na_2SO_3$ only |
| $YH_6$-I28 | (SEQ ID N: 3) | 0.03 | 0 |
| $YGH_6$-I28 | (SEQ ID NO: 4) | 0.01 | 0 |
| $YGYGH_6$-I28 | (SEQ ID NO: 5) | 0.04 | 0 |
| $H_6GY$-I28 | (SEQ ID NO: 6) | 0.43 | 0.17 |
| $H_6GYGY$-I28 | (SEQ ID NO: 7) | 1 | 0.13 |
| $YGH_6GY$-I28 | (SEQ ID NO: 8) | 0.29 | 0.01 |
| $H_3GYGH_3$-I28 | (SEQ ID NO: 9) | 0.04 | 0.01 |
| Control (no tyr) | | 0.02 | 0 |

Example 2

Two Ligand System

As a further example, a second chelator may be formed that is capable of forming a complex with a $Ni^{++}$ HY-tag that can be conveniently coupled to synthetic polymers. An oligopeptide illustratively containing tyrosine and histidine, such as those described above, may be used as this second ligand. The peptide chelator is easily coupled to fluorescent labels. Illustratively, an inexpensive synthetic ligand may be designed by modifying the synthesis of the nitrilotriacetic acid chelator used previously (Ho et al., *Langmuir*, 1998. 14:3889-3894; Wang et al., *Nature*, 1999. 397:417-420). One approach for this is to substitute imidazole or phenolic groups for the carboxylic acid groups on NTA. It is expected that these functionalities will react with the oxidized tyrosine in the HY-tag of the protein.

Example 3

Surface Immobilization

Protein arrays are widely expected to have a dramatic impact on human health care. The proteome is much more complex than the genome because of alternative splicing and post-translational modifications and therefore contains more useful information about disease states. The ability to "profile" directly the amount and chemical state of hundreds or thousands of proteins simultaneously in blood or specific tissue samples, and to correlate protein profiles with a specific disease state would have a profound effect on clinical diagnosis. As basic biomedical research tools, protein arrays would be invaluable for mapping the protein-to-protein connections of the human proteome, for high-throughput protein functional analysis like ligand binding, for identifying new protein drug targets, for identifying disease markers, for drug screening, and more.

Figure 5:
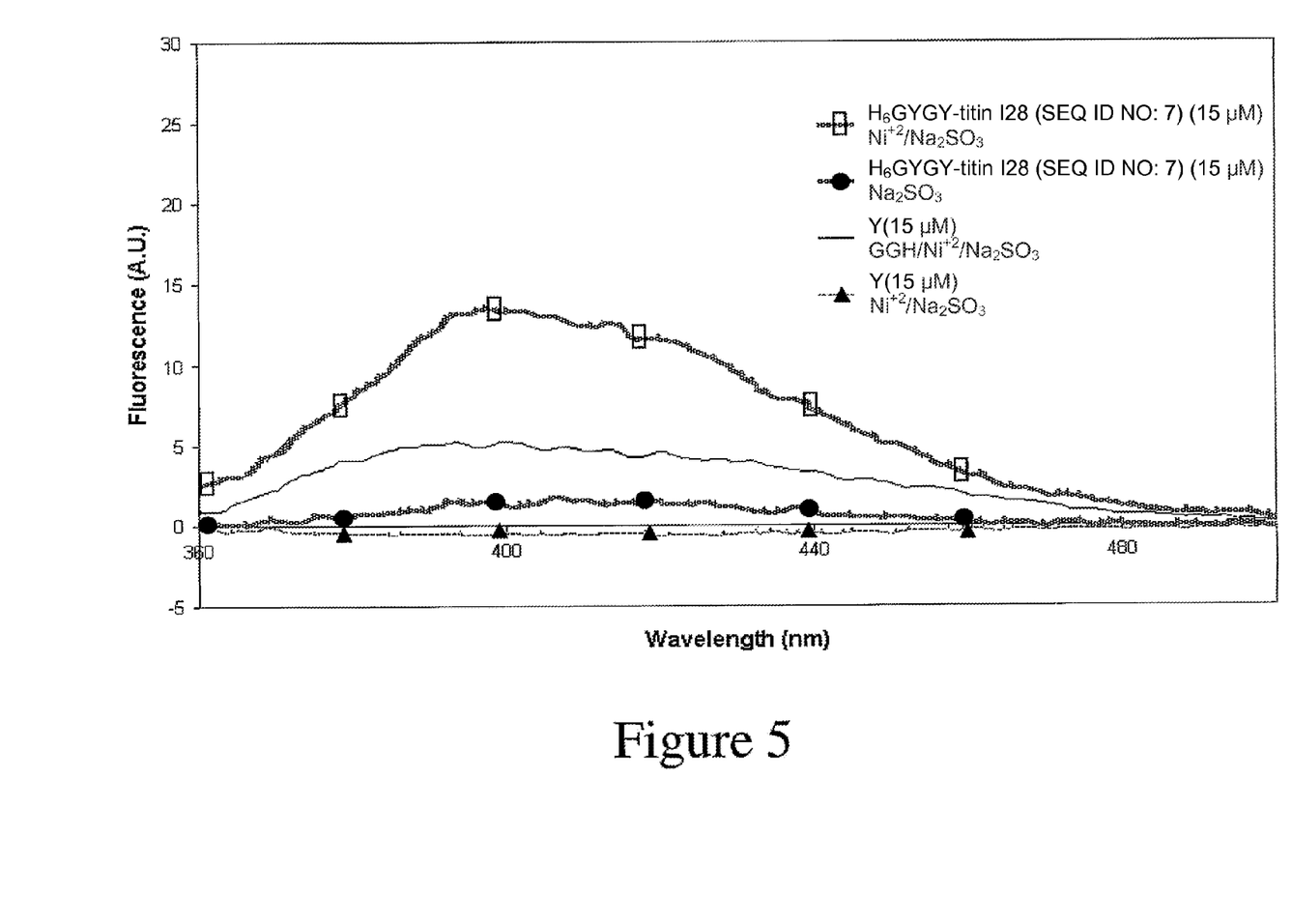
FIG. 5 shows fluorescence emission spectra of HY-tagged I28 with and without $Ni^{2+}$.
Figure 6:
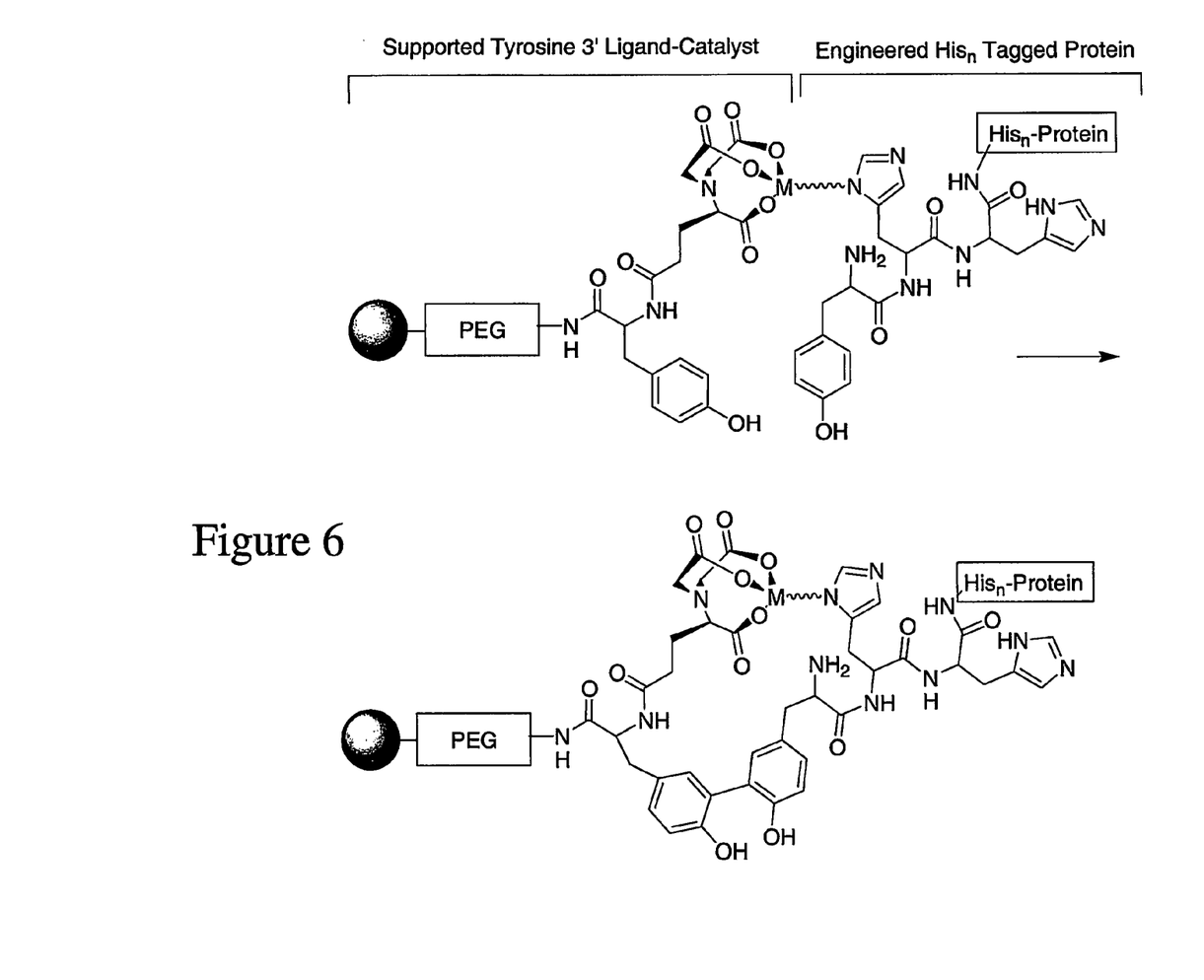
FIG. 6 shows structure of solid phase binding constructs with oxidative reactions between two tyrosines.

To test coupling of proteins to a synthetic support, nitrilotriacetic (NTA) acid was synthesized with a proximal tyrosine residue on PEGylated polystyrene beads (FIG. 5). The $H_6$YGYG-I28 (SEQ ID NO:7) protein was immobilized on the surface of the beads by Ni(II) or Cu(II) chelation through the NTA group. Some samples were oxidized with $H_2O_2$. The amount of protein bound to the beads was determined for each condition. To determine if the protein crosslinked covalently to the beads, bead bound protein was measured after washing the beads with EDTA, a chelating agent that disrupts Ni(II)-NTA-his-tag bonds. Without metal ion, I28 did not bind to the beads (Table II). In the presence of Ni(II) or Cu(II) protein was bound to the beads, with about 3× more protein bound with Ni(II) than Cu(II). EDTA stripped the protein off the beads with both metals, as expected. On the other hand, Cu(II) samples oxidized with $H_2O_2$ had bead bound protein that was not stripped by EDTA in about the same amount as the unoxidized and unstripped samples. Although preliminary, the results suggest that covalent bonds were formed between the I28 his-tyr-tags and the tyr-NTA groups on the bead surface.

TABLE II relative $H_6$YGYG-I28 bound to tyr-NTA beads.

| Sample | no EDTA | EDTA |
|---|---|---|
| No metal | 0 | — |
| Ni(II) | 1.0 ± 0.38 | 0 |
| Cu(II) | 0.33 ± 0.04 | 0.03 |
| Cu(II)/$H_2O_2$ | — | 0.32 ± 0.06 |
| $H_2O_2$ | — | 0 |

Together with the literature precedents, the HY-tagged I28 crosslinking and the surface immobilization results demonstrate that, in principle, a metal complex between two chelators will catalyze crosslinking between strategically placed phenolic groups (tyrosines) in the presence of a suitable oxidant. These results are distinct in several respects from the earlier reports of $his_6$-tag mediated crosslinking (Fancy, D. A., et al., *Chem Biol*, 1996. 3(7): p. 551-9). First, titin I28 domains do not naturally associate in solution. Second, the position of the tyr residues relative to the $his_6$-tag is shown to be a major factor in crosslinking efficiency. Third, the technique has been extended to crosslinking a peptide chelator to a surface-bound synthetic chelator. It is expected that the HIS-tag, which is nearly ubiquitous on recombinant proteins, can be used generally as a convenient site for site-specific conjugation, crosslinking, and immobilization of proteins.

Example 4

Protein Hydrogels

Utility for protein encapsulation and protein-based hydrogels is demonstrated by coupling the synthetic chelator to a monomer. The coupled monomer may then be copolymerized with acrylamide in a manner analogous to earlier work on hybrid hydrogels crosslinked with I28 domains. Chen et al., *Bioconjugate Chem.*, 11:734-740 (2000). Hydrogel formation is initiated through metal coordination bonds, and is then converted to covalent bonds. Covalent bond formation is demonstrated by evaluating hydrogel structure under conditions that disrupt metal coordination bonds. Double HY-tagged will polymerize. Novel protein materials will be created by crosslinking single and mixed double HY-tagged protein domains. These novel protein block copolymers may have unique properties. A possible application is use as a biocompatible, water-based surgical or dental adhesive. Such adhesives could be made up of polymer, protein/polymer, or simply protein compositions applied to a wound or tooth which could then be cured by the application of a mild oxidant as a curing agent. In some embodiments, especially those utilizing peroxides, such glues would sterilize the wound to which they are applied. Further, the protein used could be specifically designed to meet immunological tolerances and could include human proteins in part or whole.

The instant invention could also be used in encapsulating proteins, cells, microbes, viruses, etc., through the formation of hydrogels containing the desired particles.

Example 5

DNA Conjugates

DNA Conjugates would often take the form of DNA-chips covered with thousands of differing sequences. By attaching a polynucleotide to a ligand as described herein, such will interact with HY-tagged target proteins and allow bonding. This would allow specific proteins to be addressed/targeted to specific DNAs, or even protein sequences on a surface, and then to be covalently bound there.

Similarly, protein arrays such as those using PPO triblock pluronics with exposed (to the aqueous phase) PEO for preventing denaturing on surfaces could be used with the method of the instant invention. These would show additional usefulness since they allow for the specific orientation of the surface proteins.

Example 6

Chelators

Most chelators provide "space" for up to four coordination bonds. In one embodiment, the illustrative synthetic chelators discussed herein illustratively have capacity to form at least six of such bonds in order to form the complex needed and to cause covalent bond formation from the coordination bond in response to exposure to a mild oxidant as described herein. Four of the sites are used by the chelator, thus leaving two to form coordination bonds with the HY-tags. Illustratively, the chelators contain or are in close proximity to a phenolic functional group. Other functional groups for oxidative crosslinking may be used.

All patents and other publications cited herein are expressly incorporated by reference.

Although the invention has been described in detail with reference to certain preferred embodiments, variations and modifications exist within the scope and spirit of the invention as described and defined in the following claims.

The invention claimed is:

1. A method of crosslinking a first and a second moiety comprising the steps of:
providing a first moiety having a covalently attached first metal ligand and at least one phenolic group or phenolic derivative thereof;
providing a second moiety comprising fluorescien or fluorescien-containing derivative thereof having a covalently attached second metal ligand to the second moiety and at least one phenolic group or phenolic derivative thereof;
adding a coordinating metal ion to a reaction mixture containing the first moiety and the second moiety, thereby forming a metal coordination complex between the metal ion and each of the first and the second metal ligands, wherein the coordination complex provides said phenolic groups and/or phenolic derivatives thereof of the first and second moieties at a distance sufficient for crosslinking there between; and
exposing the metal coordination complex to an oxidizing agent, thereby covalently crosslinking the first moiety to the second moiety by the phenolic groups and/or the phenolic derivatives thereof.

2. The method of claim 1, wherein the metal coordination complex activates the oxidizing agent.

3. The method of claim 1, wherein the oxidizing agent is activated by a metalloenzyme.

4. The method of claim 3, wherein the metalloenzyme is selected from the group consisting of a peroxidase, a tyrosinase, a laccase, and a catechol oxidase.

5. The method of claim 4, wherein the peroxidase is horseradish peroxidase.

6. The method of claim 1, wherein the oxidizing agent is generated electrochemically at a surface of an electrode.

7. The method of claim 1, wherein the phenolic groups or phenolic derivatives are each selected from the group consisting of tyrosine, dihydroxyphenylalanine, and polyphenolic compounds.

8. The method of claim 1, wherein the second moiety comprises at least one phenolic group positioned such that in the metal coordination complex the phenolic group is located between 1 and 100 angstroms from the metal ion.

9. The method of claim 1, wherein the first moiety comprises at least one phenolic group positioned such that in the metal coordination complex the phenolic group is located between 1 and 100 angstroms from the metal ion.

10. The method of claim 9, wherein the phenolic group is a tyrosine residue located on the first moeity.

11. The method of claim 10, wherein the phenolic group is a tyrosine residue located within the metal ligand on the first moiety and positioned such that in the metal coordination complex the tyrosine is located between the metal ion and a first polymer.

12. The method of claim 1, wherein the covalent crosslink is dityrosine and isomers thereof.

13. The method of claim 1, wherein the first moiety is a first synthetic polymer moiety covalently attached to said first metal ligand and to said phenolic group or phenolic derivative thereof; and/or the second moiety is a second synthetic polymer moiety covalently attached to said second metal ligand and to said phenolic group or phenolic derivative thereof; and wherein the synthetic polymer in the first and/or second moiety is selected from the group consisting of polyethylene glycol, polypropylene glycol, polyesters, and polyethylene glycol and polypropylene glycol block copolymers.

14. The method of claim 1, wherein the first moiety is a polymer.

15. The method of claim 1, wherein one of the first and second moieties further comprises an attachment to a solid surface.

16. The method of claim 15, wherein the solid surface is selected from the group consisting of a polymer, a metal, a ceramic, a composite, a biopolymer, a bioceramic, and a colloidal particle.

17. The method of claim 16, wherein the solid surface is a metal surface and which surface is further coated with a polymer, said polymer attaching said metal surface to said first or second moiety.

18. The method of claim 16, wherein the solid surface is a colloidal particle and the colloidal particle is composed of a material selected from the group consisting of gold, silver, silica, semiconductors, fluorescent semiconductors, polystyrene, polymeric micelles, dendrimers, liposomes, and viruses.

19. The method of claim 16, wherein the surface is a colloidal gold particle and the colloidal particle has a diameter of from 1 nm to 100 μm.

20. The method of claim 1, wherein both the first and second moieties are solid surface attached moieties.

21. The method of claim 20, wherein the solid surfaces of the first and second solid surface attached moieties are different solid surfaces and wherein the crosslinking adheres the different solid surfaces therethrough.

22. The method of claim 21, wherein each of the solid surfaces are biological tissues.

23. The method of claim 21, wherein each of the solid surfaces are independently selected from the group consisting of polymers, metals, ceramics, composites, biopolymers, bioceramics, colloidal particles, and combinations thereof.

24. The method of claim 23, wherein at least one of the solid surfaces is a colloidal particle, and the colloidal particle is composed of a material selected from the group consisting of gold, silver, silica, semiconductors, fluorescent semiconductors, polystyrene, polymeric micelles, dendrimers, liposomes, and viruses.

25. The method of claim 24, wherein the colloidal particle has a diameter from 1 nm to 100 μm.

26. The method of claim 1, wherein at least one of the first moiety and the second moiety is biodegradable.

27. The method of claim 1, wherein at least one of the first moiety and the second moiety further comprises a therapeutic agent.

28. The method of claim 27, wherein the therapeutic agent is a protein.

29. The method of claim 1, wherein the first moiety is a His-Tyr tag (HY-tag).

30. The method of claim 29, wherein the first moiety contains a plurality of tyrosine residues interdispersed throughout HY-tag.

31. The method of claim 29, wherein the HY-tag comprises a plurality of histidine residues.

32. The method of claim 1, wherein the coordinating metal ion is selected from the group consisting of nickel, copper, cobalt, gadolinium, iron, osmium, palladium, rhodium, ruthenium, samarium, selenium, silver, strontium, tantalum, thulium, tin, tungsten, vanadium, yttrium, and zinc.

* * * * *

```
                         SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: completely synthesized

<400> SEQUENCE: 1

His His His His His His
1               5

<210> SEQ ID NO 2
<211> LENGTH: 6
<212> TYPE: PRT
<213> ORGANISM: Artificial Sequence
<220> FEATURE:
<223> OTHER INFORMATION: completely synthesized
<220> FEATURE:
<223> OTHER INFORMATION: glutathione S-transferase at C-terminus

<400> SEQUENCE: 2

His His His His His His
1               5

<210> SEQ ID NO 3
<211> LENGTH: 7
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 3

Tyr His His His His His His
1               5

<210> SEQ ID NO 4
<211> LENGTH: 8
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 4

Tyr Gly His His His His His His
1               5

<210> SEQ ID NO 5
<211> LENGTH: 10
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 5

Tyr Gly Tyr Gly His His His His His His
1               5                   10
```

```
<210> SEQ ID NO 6
<211> LENGTH: 8
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 6

His His His His His His Gly Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 7

His His His His His His Gly Tyr Gly Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: completely synthesized
<220> FEATURE:
<223> OTHER INFORMATION: linkage to a monomeric titin I28 Ig domain

<400> SEQUENCE: 8

Tyr Gly His His His His His His Gly Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: completely synthesized

<400> SEQUENCE: 9

His His His Gly Tyr Gly His His His
1               5
```